(12) United States Patent
Nitzan (10) Patent No.: US 12,350,043 B2
(45) Date of Patent: Jul. 8, 2025

(54) METHOD FOR MEASUREMENTS OF OXYGENATED AND DE-OXYGENATED HEMOGLOBIN CONCENTRATION

(71) Applicant: JERUSALEM COLLEGE OF TECHNOLOGY, Jerusalem (IL)

(72) Inventor: Meir Nitzan, Bet El (IL)

( * ) Notice: Subject to any disclaimer, the term of this patent is extended or adjusted under 35 U.S.C. 154(b) by 1039 days.

(21) Appl. No.: 17/289,744

(22) PCT Filed: Nov. 11, 2019

(86) PCT No.: PCT/IL2019/051229
§ 371 (c)(1),
(2) Date: Apr. 29, 2021

(87) PCT Pub. No.: WO2020/095312
PCT Pub. Date: May 14, 2020

(65) Prior Publication Data
US 2022/0000400 A1    Jan. 6, 2022

Related U.S. Application Data

(60) Provisional application No. 62/758,588, filed on Nov. 11, 2018.

(51) Int. Cl.
*A61B 5/1455* (2006.01)
*A61B 5/00* (2006.01)
(Continued)

(52) U.S. Cl.
CPC ...... *A61B 5/14551* (2013.01); *A61B 5/02416* (2013.01); *A61B 5/7239* (2013.01);
(Continued)

(58) Field of Classification Search
CPC ............ A61B 5/14551; A61B 5/02416; A61B 5/7239; A61B 5/024; A61B 5/0295;
(Continued)

(56) References Cited

U.S. PATENT DOCUMENTS 5,729,333 A * 3/1998 Osten ................. A61B 5/14535
356/39
5,931,779 A * 8/1999 Arakaki ............... A61B 5/1459
600/476

(Continued)

OTHER PUBLICATIONS

Yang et al., "Quantitative measurement of muscle oxygen saturation without influence from skin and fat using continuous-wave near infrared spectroscopy," Optics Express 15: 13715-13730 (2007) (Year: 2007).*

*Primary Examiner* — Jennifer Robertson
*Assistant Examiner* — Jonathan Drew Moroneso
(74) *Attorney, Agent, or Firm* — Patshegen IP; Moshe Pinchas (57) ABSTRACT

A method for the measurement of oxygenation level of blood in a tissue. The method includes emitting on a tissue light having a wavelength range in which oxygenated hemoglobin has a first extinction coefficient and de-oxygenated hemoglobin has a second extinction coefficient, and wherein one of the first and second extinction coefficients changes monotonically as a function of wavelength while the other one of the first and second extinction coefficients is substantially constant with respect to the one of the first and second extinction coefficients. The method further includes detecting a transmitted spectrum of light transmitted through the tissue, measuring a differentiating parameter expressing a change in at least one parameter of the emitted spectrum with respect to same parameter in the transmitted spectrum, and determining an oxygenation level of blood in the tissue, wherein the oxygenation level corresponds to a value of the measured differentiating parameter.

23 Claims, 3 Drawing Sheets

(51) Int. Cl.
  *A61B 5/024*    (2006.01)
  *A61B 5/0295*   (2006.01)
  *A61B 5/08*     (2006.01)
  *A61B 5/145*    (2006.01)
  *G01S 15/89*    (2006.01)

(52) U.S. Cl.
  CPC ............. *A61B 5/024* (2013.01); *A61B 5/0295* (2013.01); *A61B 5/0816* (2013.01); *A61B 5/145* (2013.01); *A61B 5/1455* (2013.01); *A61B 5/72* (2013.01); *A61B 2560/0223* (2013.01); *G01S 15/899* (2013.01)

(58) Field of Classification Search
  CPC ..... A61B 5/0816; A61B 5/145; A61B 5/1455; A61B 5/72; A61B 2560/0223; G01S 15/899

See application file for complete search history.

(56) References Cited

U.S. PATENT DOCUMENTS

| | | | | |
|---|---|---|---|---|
| 6,473,632 | B1* | 10/2002 | Myers | G01N 21/3504 600/328 |
| 7,400,918 | B2* | 7/2008 | Parker | B65H 23/18 600/323 |
| 7,532,919 | B2* | 5/2009 | Soyemi | G01N 33/4925 600/323 |
| 7,909,768 | B1* | 3/2011 | Turcott | A61B 5/1455 600/481 |
| 9,848,807 | B2* | 12/2017 | Lamego | A61B 5/02416 |
| 10,420,457 | B2* | 9/2019 | Chiba | A61B 1/0638 |
| 2008/0208019 | A1* | 8/2008 | Nitzan | A61B 5/14551 600/323 |
| 2009/0076354 | A1* | 3/2009 | Huiku | A61B 5/14551 600/331 |
| 2011/0205535 | A1* | 8/2011 | Soller | A61B 5/1455 356/300 |
| 2013/0274573 | A1* | 10/2013 | McCully | A61B 5/14546 600/328 |
| 2018/0177459 | A1* | 6/2018 | Eletr | A61B 5/02125 |
| 2020/0163602 | A1* | 5/2020 | Pareddy | A61B 5/6807 |

* cited by examiner

METHOD FOR MEASUREMENTS OF OXYGENATED AND DE-OXYGENATED HEMOGLOBIN CONCENTRATION

FIELD OF INVENTION

The presently disclosed subject matter relates to a method for measurements of oxygenated and de-oxygenated hemoglobin concentration using light emitting diodes.

BACKGROUND ART

1. Yoshiya I, Shimady Y and Tanake K. Spectrophotometric monitoring of arterial oxygen saturation on the fingertip. Med. Biol. Eng. Comput. 18:27-32 (1980).
2. Wieben O. Light absorbance in pulse oximetry. In: Design of Pulse Oximeters. J. G. Webster, editor. Institute of Physics Publishing, Bristol, pp. 40-55, (1997).
3. Guiton A C and Hall J E. Textbook of Medical Physiology, W.B. Webster Company, Philadelphia Ch. 40, (1996).
4. Matcher S J, Signal quantification and localization in tissue near-infrared spectroscopy. In Handbook of Optical Biomedical Diagnostics, Tuchin V V Editor, SPIE Press, Bellingham, Washington, Ch. 9. (2002).
5. Nicklin S E, Hassan I A, Wickramasinghe Y A and Spencer S A, The light still shines, but not that brightly? The current status of prenatal near infrared spectroscopy. Arch. Dis. Child Fetal Neonatol. Ed. 88:F263-F268 (2003).
6. Fantini S and Francheschini M A. Frequency-domain Techniques for tissue spectroscopy and imaging. In Handbook of Optical Biomedical Diagnostics, Tuchin V V Editor, SPIE Press, Bellingham, Washington, Ch. 7 (2002).
7. Delpy D T, Cope M, van der Zee P. Arridge S, Wray S and Wyatt J. Estimation of optical pathlength through tissue from direct time of flight measurement. Phys Med Biol 33:1433-1442. (1988).
6. Duncan A, Meek J H, Clemence M, et al. Optical pathlength measurements on adult head, calf and forearm and the head of the newborn infant using phase resolved optical spectroscopy. Phys Med Biol 1995; 40:295e304.
7. Wyatt J S, Cope M, Delpy D T, et al. Measurement of optical pathlength for cerebral near infrared spectroscopy in newborn infants. Dev Neurosci 1990; 12:140e4. 8. Van der Zee P, Cope M, Arridge S R. Experimentally measured optical pathlengths for the adult head, calf and forearm and the head of the newborn infant as a function of the interoptode spacing. Adv Exp Med Biol 1992; 316:143c53.
8. Yoxall C W and Weindling A M, Measurements of venous oxyhemoglobin saturation in the adult human fore arm by near infrared spectroscopy with venous occlusion, Med. Biol. Eng. Comput. 35:331-336 (1997).
9. Ferreira L F, Hueber D M and Barstow T J. Effects of assuming constant optical scattering on measurements of muscle oxygenation by near-infrared spectroscopy during exercise. J Appl Physiol 102: 358-367 (2007).
10. A. Babchenko, B. Khanokh, Y. Shomer and M. Nitzan. A fiber-optic sensor for the measurement of the respiratory chest circumference changes. J. Biomed. Optics. 4:224-229 (1999).
11. Schowalter J S. Calibration. In: Design of Pulse Oximeters. J. G. Webster, editor. Institute of Physics Publishing, Bristol, Ch. 10 (1997).
12. Mendelson Y and Ochs B D, Noninvasive pulse oximetry utilizing skin reflectance photoplethysmography. IEEE Tr BME 35: 798-805 (1988)
13. Nitzan M, Babchenko A, Khanokh B, and Taitelbaum H, The measurement of oxygen saturation in venous blood by dynamic near IR spectroscopy. J. Biomed. Optics. 5:155-162 (2000).
14. Nitzan M and Taitelbaum H. The measurement of oxygen saturation in arterial and venous blood. IEEE Instrumentation and Measurement Magazine, 11:9-15 (2008).
15. Skov L, Pryds O, Greisen G and Lou H. Estimation of cerebral venous saturation in newborn infants by near infrared spectroscopy. Ped. Res. 33:52-55 (1993).
16. Uilkema R J, Bastiaan A and Groeneveld J. Correlates of thenar near-infrared spectroscopy-derived tissue O2 Saturation after cardiac surgery. Interactive Cardiovasc. Thoracic Surg. 6:265-269 (2007).
17. McCully K K, Halber C and Posner J D. Exercise-induced changes in oxygen saturation in the calf muscles of elderly subjects with peripheral vascular disease. J. Gerontol. 49: B128-B134 (1994).
18. Mohler E R, Lech G, Supple G E, Wang H and Chance B, Impaired Exercise-induced blood volume in type 2 diabetes with or without peripheral arterial disease measured by continuous-wave near-infrared spectroscopy. Diabetes Care, 29:1856-1859 (2006).
22. Delpy D T and Cope M. Quantification in tissue near-infrared spectroscopy. Phil Trans. R. Soc. Lond. B 352: 649-659 (1997).
23. Wolf M, Ferrari M and Quaresima V, Progress of near-infrared spectroscopy and topography for brain and muscle clinical applications. J. Biomed. Optics, 12:062104-1-14 (2007)
24. Hamaoka T, Katsumura T, Murase N, Nishio S, Osada T, Sako T, Higuchi H, Kurosawa Y, Shimomitsu T, Miwa M and Chance B. Quantification of ischemic muscle deoxygenation by near-infrared time-resolved spectroscopy. J. Biomed. Optics 5: 102-105 (2000).
25. Elwell C E, Matcher S J, Tyzszcuk L, Mcck J H and Delpy D T. Measurement of cerebral venous saturation in adults using near infrared spectroscopy. Adv. Exp. Med. Biol. 411:453-460 (1997).
26. De Blasi R A, Ferrari M, Natali A, Conti G. Mega A and Gaspareto A. Noninvasive measurement of forearm blood flow and oxygen consumption by near infrared spectroscopy. J. Appl. Physiol. 76 (3): 1388-1393 (1994).
30. Duncan A, Meek J H, Clemence M, Elwell C E, Tyszczuk L, Cope M and Delpy D T. Optical pathlength measurements on adult head, calf and forearm and the head of the newborn infant using phase resolved spectroscopy. Phys. Med. Biol. 40:295-304 (1995).

BACKGROUND OF INVENTION

Transfer of oxygen from the lungs to the tissue cells is done mainly via the hemoglobin molecules in the red blood cells (about 98% of the total oxygen content in blood is bound to hemoglobin). Oxygen saturation in the blood, $SO_2$, is the ratio of oxygenated hemoglobin concentration CO to total hemoglobin concentration in the blood, CO+CD, where CD is the de-oxygenated hemoglobin concentration. $SO_2$ in arterial blood, $SaO_2$, has clinical and physiological significance, since it depends on the adequacy of the ventilation and respiratory function. $SaO_2$ is routinely assessed non-invasively by pulse oximetry (1,2)—an optical technique, shortly described below—and its normal values are 94-98%.

Even after transferring oxygen to the tissue in the capillaries, most of the hemoglobin in venous blood is still oxygenated: normal values of the oxygen saturation in the systemic veins is 70-80% (3). Venous blood oxygen saturation, $SvO_2$, also has physiological and clinical diagnostic significance, because the difference between $SaO_2$ and $SvO_2$ is related to the oxygen consumption in tissue. $SvO_2$ increases with $SaO_2$ and with tissue blood flow and decreases with increasing tissue metabolism.

Figure 1:
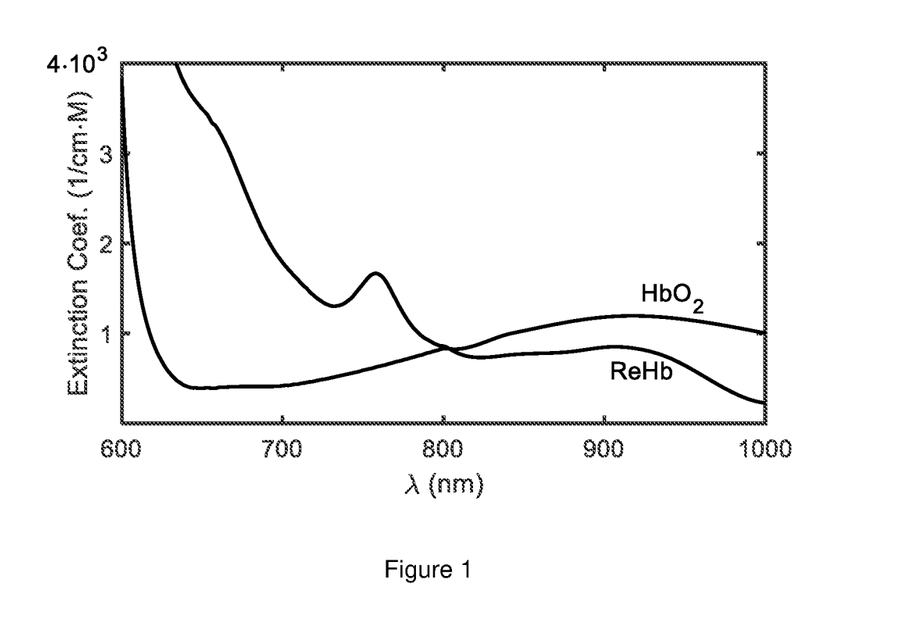
FIG. 1 is a prior art graph illustration of the extinction coefficients of the oxyhemoglobin and deoxyhemoglobin as a function of the wavelength, in the red and near-infrared regions.

The absorption constant of a blood sample depends on the hemoglobin concentration in the blood sample. The extinction coefficient s of the hemoglobin is defined as the absorption constant of the blood sample divided by the molar concentration of the hemoglobin in the sample. FIG. 1 shows the extinction coefficients as a function of wavelength for oxygenated (hereinafter $HbO_2$) and de-oxygenated (hereinafter ReHb) hemoglobin, in the red and near infrared regions. The hemoglobin in either arterial or venous blood is a mixture of $HbO_2$ with extinction coefficient so and ReHb with extinction coefficient $\varepsilon_D$ and the total extinction coefficient E in the blood is related to its oxygen saturation, $SO_2$ (which can be either $SaO_2$ or $SvO_2$) by:

$$\varepsilon = \varepsilon_O SO_2 + \varepsilon_D(1-SO_2) = \varepsilon_O + SO_2(\varepsilon_O - \varepsilon_D) \quad \text{(hereinafter Equation [1])}$$

The transmitted light intensity, $I_t$, through a tissue sample of width d which includes vessels with whole blood is given by the modified Beer-Lambert Law:

$$I_t = I_0 e^{-G-\varepsilon Cl} \quad \text{(hereinafter Equation [2a])}$$

or as:

$$\ln\left(\frac{I_0}{I_t}\right) = G + \varepsilon Cl, \quad \text{(hereinafter Equation [2b])}$$

where $I_0$ is the incident light intensity, and l is the effective optical path-length, which is greater than d because of the effect of scattering, (the ratio l/d is named the differentiating pathlength factor—DPF). G is an attenuation factor due to absorption and scattering in the tissue, that was added to the hemoglobin absorption factor $\varepsilon Cl$I, where C is the concentration of the hemoglobin in the tissue (Delpy 1988, Edwards 1993, Matcher 2002).

Tissue near infrared spectroscopy (NIRS) is a noninvasive optical technique for the determination of oxygenation in the total blood in tissue, which includes arteries, capillaries and veins. NIRS can evaluate the concentrations of $HbO_2$ and ReHb in the tissue from the measurement of light transmission at several wavelengths. As described above, the light transmission through the tissue is affected not only by absorption but also by scattering, and several techniques have been developed for the isolation of the absorption constant from the scattering effects, including time resolved spectroscopy, frequency-domain spectroscopy and spatially resolved spectroscopy (4-6,8,9,15-30).

In the latter technique, light transmission is measured as a function of the distance between the light-source and the detector for different wavelengths. By using an appropriate mathematical model, the dependence of light transmission on the distance between the light-sources and the detectors can be related to the absorption constant and scattering constant of the tissue, enabling the derivation of hemoglobin concentration and tissue $SO_2$. These techniques, which are generally based on a semi-infinite homogenous model, show good agreement in studies on infinite homogenous phantoms, but when applied to examinations on living tissue exhibit significant discrepancy. Low accuracy and low reproducibility limit the effective use of NIRS in clinical environment.

The wavelength region used in NIRS is selected in the near infrared because of the greater transmission in the near infrared relative to the red region, where the extinction coefficient of the de-oxygenated hemoglobin is greater than $1.5\ cm^{-1} \cdot M^{-1}$. NIRS is mainly important for the measurement of ReHb and $HbO_2$ concentration in the brain, and the technique requires efficient light transmission through a distance of several cm in the brain.

In pulse oximetry, which mainly utilize light transmission through the finger, the selection of one of the wavelengths in the red region is because of the great difference in extinction coefficient between ReHb and $HbO_2$.

Light emitted from a typical LED which has a bandwidth of tens of nanometers undergoes spectral change when propagating through tissue, due to wavelength-dependent absorption and scattering. Since both the absorption and scattering constants depend upon the wavelength, photons of different wavelengths undergo different attenuation. Hence, the shape of the spectrum of light that propagates through tissue is expected to differ from that of the light emitted by the LED. The effect is particularly prominent in LEDs that emit light in wavelength region in which the curve of the ReHb or $HbO_2$ extinction coefficients versus wavelength have a steep slope. Two wavelength regions with significant slope of the ReHb or $HbO_2$ extinction coefficients curve are designated in FIG. 2. In the wavelength-region of 640-700 nm, the extinction coefficient curve for ReHb steeply decreases while that for $HbO_2$ only increases slightly with light wavelength. In the 820-880 nm wavelength region, the $HbO_2$ extinction coefficient curve increases significantly with the wavelength, while the ReHb extinction coefficient curve is almost independent on the wavelength.

SUMMARY OF INVENTION

There is provided in accordance with an aspect of the presently disclosed subject matter a method for the measurement of oxygenation level of blood in a tissue. The method includes emitting on a tissue light having a wavelength range in which oxygenated hemoglobin has a first extinction coefficient and de-oxygenated hemoglobin has a second extinction coefficient, and wherein one of the first and second extinction coefficients changes monotonically as a function of wavelength while the other one of the first and second extinction coefficients is substantially constant with respect to the one of the first and second extinction coefficients.

The method further includes detecting a transmitted spectrum of light transmitted through the tissue, measuring a differentiating parameter expressing a change in at least one parameter of the emitted spectrum with respect to same parameter in the transmitted spectrum, and determining an oxygenation level of blood in the tissue, wherein the oxygenation level corresponds to a value of the measured differentiating parameter.

Determining oxygenation level of blood in a tissue can include one of the following parameters of the blood in tissue: concentration of oxygenated hemoglobin, concentration of deoxygenated hemoglobin, oxygen saturation.

The differentiating parameter can include measuring a difference between wavelength at the peak of the emitted spectrum and wavelength at the peak of the transmitted spectrum.

The differentiating parameter can include measuring a difference between weighted mean wavelength of the emitted spectrum and weighted mean wavelength of the transmitted spectrum. The differentiating parameter can include measuring a difference in mean extinction coefficient for the emitted and transmitted spectra.

The step of determining an oxygenation level of blood in the tissue can be carried out by predetermined calibration comparing derived values of the differentiating parameter and a corresponding oxygenation level obtained by means of another method.

The calibration can be obtained by near infrared spectroscopy.

The calibration can be obtained by venous and/or arterial pulse oximetry.

The step of measuring the differentiating parameter can be measuring $$\ln\left(\frac{I_0}{I_t}\right)(\lambda)$$

and the step of determining an oxygenation level of blood in the tissue can be carried out by utilizing the equation:

$$\ln\left(\frac{I_0}{I_t}\right)(\lambda) = G(\lambda) + \varepsilon_D C_D l_R(\lambda) + \varepsilon_O C_O l_{IR}(\lambda)$$

The step of determining an oxygenation level of blood in the tissue can be slope of $$\ln\left(\frac{I_0}{I_t}\right)(\lambda)$$

as a function of $\varepsilon_O(\lambda)$ or $\varepsilon_O(\lambda)$.

The emitted spectrum can be in the region of 640-720 nm.
The emitted spectrum can be in the region of 650-670 nm.
The emitted spectrum can be in the region of 820-880 nm.

There is provided in accordance with an aspect of the presently disclosed subject matter a device for the measurement of oxygenation level of blood in a tissue. The device includes a light source for emitting on a tissue light having a wavelength range in which oxygenated hemoglobin has a first extinction coefficient and de-oxygenated hemoglobin has a second extinction coefficient, and wherein one of the first and second extinction coefficients changes monotonically as a function of wavelength while the other one of the first and second extinction coefficients is substantially constant with respect to the one of the first and second extinction coefficients.

The device further includes a detector for detecting a transmitted spectrum of light emitted from the light source and transmitted through the tissue, and a controller configured for measuring a differentiating parameter expressing a change in at least one parameter of the emitted spectrum with respect to same parameter in the transmitted spectrum; the controller being further configured for determining an oxygenation level of blood in the tissue such that the oxygenation level corresponds to a value of the measured differentiating parameter.

Determining oxygenation level of blood in a tissue can include one of the following parameters of the blood in tissue: concentration of oxygenated hemoglobin, concentration of deoxygenated hemoglobin, oxygen saturation.

The differentiating parameter can include measuring a difference between wavelength at the peak of the emitted spectrum and wavelength at the peak of the transmitted spectrum.

The differentiating parameter can include measuring a difference between weighted mean wavelength of the emitted spectrum and weighted mean wavelength of the transmitted spectrum.

The differentiating parameter can include measuring a difference in mean extinction coefficient for the emitted and transmitted spectra.

The controller can include predetermined calibration data between derived values of the differentiating parameter and a corresponding oxygenation level obtained by means of another device.

The other device can utilize a method of near infrared spectroscopy.

The other device can be venous and/or arterial pulse oximetry.

The differentiating parameter can be $$\ln\left(\frac{I_0}{I_t}\right)(\lambda)$$

and the controller can be configured for determining an oxygenation level of blood in the tissue by utilizing the equation:

$$\ln\left(\frac{I_0}{I_t}\right)(\lambda) = G(\lambda) + \varepsilon_D C_D l_R(\lambda) + \varepsilon_O C_O l_{IR}(\lambda)$$

The controller can be configured for determining an oxygenation level of blood in the tissue is slope of $$\ln\left(\frac{I_0}{I_t}\right)(\lambda)$$

as a function of $\varepsilon_O(\lambda)$ or $\varepsilon_O(\lambda)$.

The light source can be configured to emit light in the spectrum in the region of 640-720 nm.

The light source can be configured to emit light in the spectrum in the region of 650-670 nm.

The light source can be configured to emit light in the spectrum in the region of 820-880 nm.

Differentiating parameter as used in the specification and claims refers to a parameter expressing a change in at least one parameter of the emitted spectrum with respect to same parameter in the transmitted spectrum, i.e. at least one property of the two spectrums that differentiates between them. The differentiating parameter can be a calculated parameter which expresses changes in the spectrums for example, changes in the intensities. Alternatively, the differentiating parameter can be a calculated difference between a first value when measuring a selected parameter in the emitted spectrum and a second value when measuring the selected parameter in the transmitted spectrum. The parameter for calculating difference in values can be, for example, a difference between wavelength at the peak of the emitted spectrum and wavelength at the peak of the transmitted spectrum, a difference between weighted mean wavelength of the emitted spectrum and weighted mean wavelength of the transmitted spectrum, or a difference in mean extinction coefficient for the emitted and transmitted spectra.

BRIEF DESCRIPTION OF THE DRAWINGS

In order to understand the disclosure and to see how it may be carried out in practice, embodiments will now be described, by way of non-limiting examples only, with reference to the accompanying drawings, in which.

DESCRIPTION OF THE PREFERRED EMBODIMENTS

The presently disclosed subject matter provides a method for the measurement of oxygenation level of blood in a tissue. The method includes emitting on a tissue light having a wavelength range in which oxygenated hemoglobin has a first extinction coefficient and de-oxygenated hemoglobin has a second extinction coefficient, and wherein one of the first and second extinction coefficients changes monotonically as a function of wavelength while the other one of the first and second extinction coefficients is substantially constant with respect to the one of the first and second extinction coefficients;

The method further includes detecting a transmitted spectrum of light transmitted through the tissue and measuring a differentiating parameter expressing a change in at least one parameter of the emitted spectrum with respect to same parameter in the transmitted spectrum. Finally, oxygenation level of blood in the tissue is determined from the value of the measured differentiating parameter.

For example, if light in the red region in which there is steep declining slope of the extinction coefficient curve for deoxygenated hemoglobin is utilized, the RcHb concentration, $C_D$, is assessed by measuring changes between emitted and transmitted spectra of a LED in the red region.

Light emitted from a typical LED which has a bandwidth of tens of nanometers undergoes spectral change when propagating through tissue, due to wavelength-dependent absorption and scattering. Since both the absorption and scattering constants depend upon the wavelength, photons of different wavelengths undergo different attenuation. Hence, the shape of the spectrum of light that propagates through tissue is expected to differ from that of the light emitted by the LED. The effect is particularly prominent in LEDs that emit light in wavelength region in which the curve of the ReHb or $HbO_2$ extinction coefficients versus wavelength have a steep slope.

Figure 2:
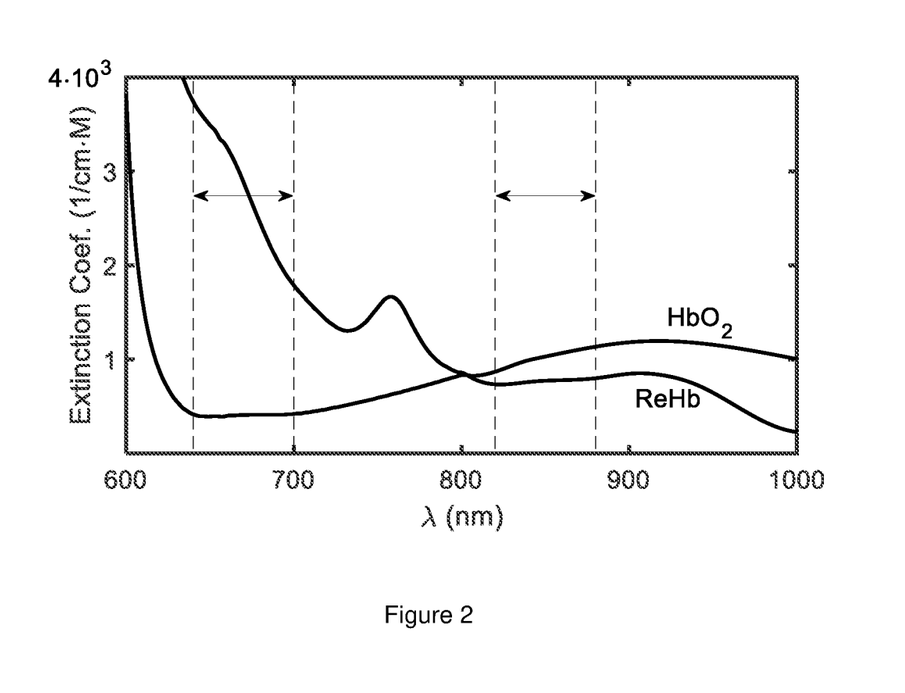
FIG. 2 is a prior art graph illustration of regions of wavelengths in which extinction coefficients of one of the oxyhemoglobin and deoxyhemoglobin is affected by wavelength changes while the extinction coefficients of the other one of the oxyhemoglobin and deoxyhemoglobin is substantially constant.

Two wavelength regions with significant slope of the ReHb or $HbO_2$ extinction coefficients curve are designated in FIG. 2. In the wavelength-region of 640-720 nm, the extinction coefficient curve for ReHb steeply decreases while that for $HbO_2$ only increases slightly with light wavelength. In the 820-880 nm wavelength region, the $HbO_2$ extinction coefficient curve increases significantly with the wavelength, while the ReHb extinction coefficient curve is almost independent on the wavelength.

Figure 3:
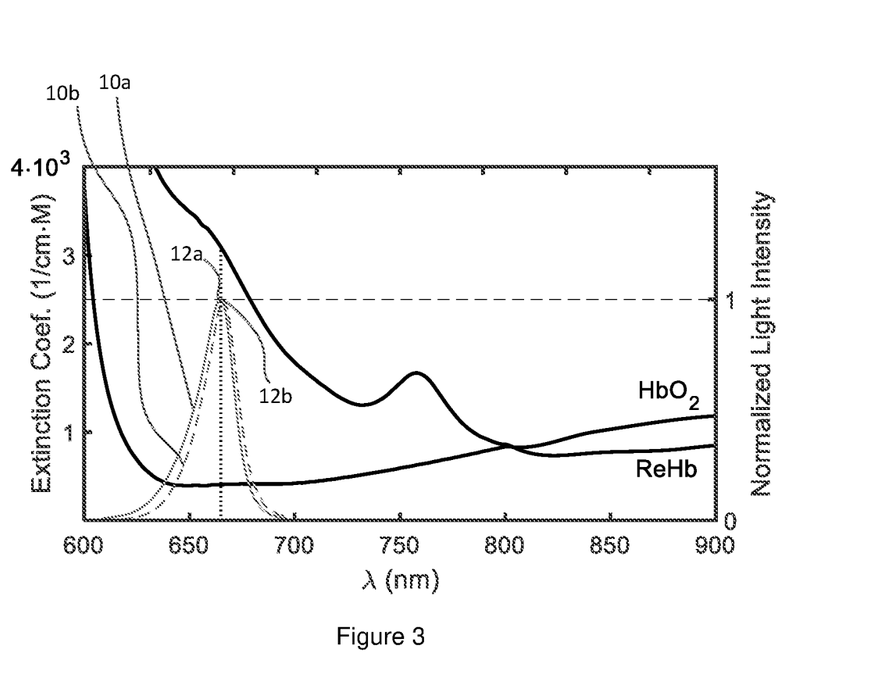
FIG. 3 is a graph illustration of an emitted and transmitted spectra of a LED, emitting light in the red region.

FIG. 3 illustrates emitted light spectrum 10a of a LED with peak wavelength at 665 nm and spectral width of several tens of nanometers, as well as the spectrum of the transmitted light 10b after being transmitted through the finger of a human subject. In this graph the two measured intensities are normalized relative to the maximal intensity for each spectrum.

As explained hereinabove, in the wavelength-region of 640-700 nm, the extinction coefficient curve for ReHb steeply decreases. Thus, the transmitted light spectrum 10b is slightly shifted towards longer wavelengths relative to the spectrum of the emitted light 10a. The ReHb extinction coefficient values for wavelengths shorter than 665 nm are higher than that for 665 nm, hence the absorption for the former is greater than that for 665 nm and the normalized transmitted intensity, shown in spectrum 10b, is smaller than the normalized emitted intensity, shown in spectrum 10a.

Similarly, when assessing the peak of emitted and transmitted spectrums 10a and 10b, photons of wavelengths slightly longer than the wavelengths at the peak intensity 12b of the transmitted spectrum 10b, experience less absorption relative to the wavelength at the peak 12a of the emitted spectrum 10a. Consequently, the wavelengths slightly longer than the wavelengths at the peak intensity 12a, after being transmitted through the finger of a human subject provide greater intensity, shown in the transmitted peak 12b. It is noted that the emitted and transmitted spectrums 10a and 10b are normalized, such that the difference in the peak intensities 12a and 12b can be assessed with respect to the effect of the extinction coefficient values only. i.e. eliminating other factors which affect the intensity of the transmitted spectrum, and which are not necessarily affected by the change in the wavelength and the extinction coefficient values.

It should be noted that in the wavelength-region of 640-700 nm, the extinction coefficient curve for $HbO_2$ only increases slightly with light wavelength (as shown in FIGS. 1 and 2), resulting in only a small increase of the normalized transmitted light intensity with shorter wavelengths relative to that for longer wavelengths. Hence, the effect of spectral change due to absorption by $HbO_2$ is much smaller than that for ReHb because of the steeper slope for the ReHb curve relative to that of $HbO_2$. Thus, although in the present illustration the selected emitted spectrum is selected such that the peak intensity is at a wavelength of 665 nm, other spectrums in the wavelength-region of 640-720 nm, may be selected to obtain information regarding the absorption by ReHb.

Figure 4:
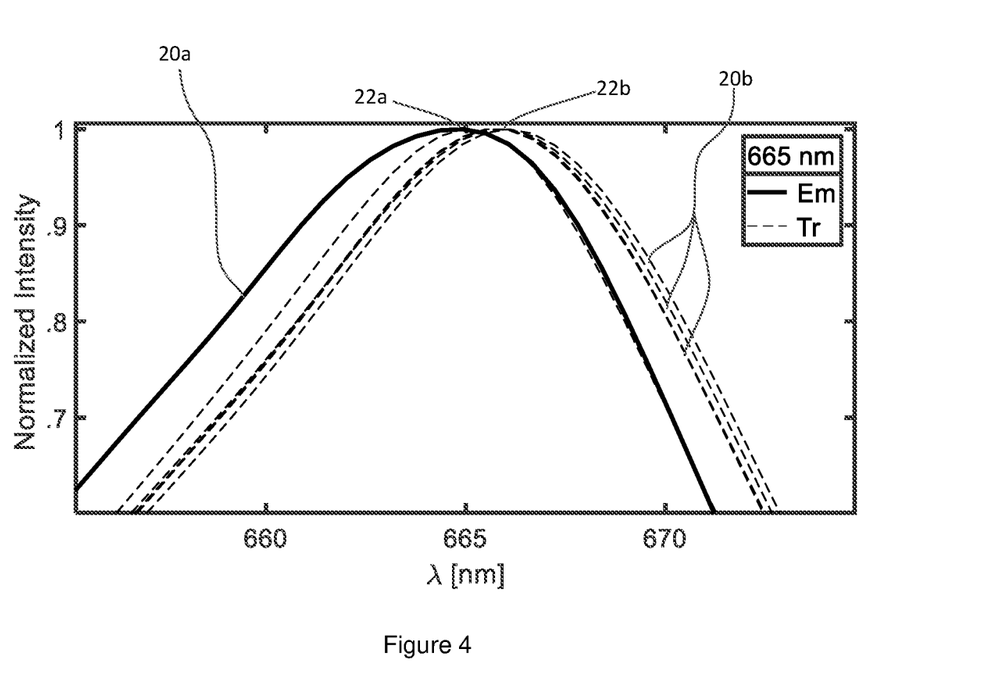
FIG. 4 is a graph illustration of an emitted spectrum of the LED in FIG. 3 in the red region and transmitted spectrum of several examinees; and, FIG. 5 is a graph illustration showing a ration between the emitted and transmitted spectra as a function of the extinction coefficients of the deoxyhemoglobin.

It is noted that the change in the normalized emitted and transmitted spectrums, may vary with respect to various examinees due to inter-subject variability of the ReHb concentration. As shown in FIG. 4 while the normalized emitted light 20a having a peak 22a in wavelength of 665 nm is constant, the normalized intensities of the transmitted light 20b experience different changes for different examinees. However, all curves of the normalized transmitted spectrum 20b are shifted with respect to the transmitted spectrum 20a in the direction towards longer wavelengths.

As explained hereinabove, this shift is due to the steeply decreasing extinction coefficient curve for ReHb in the spectrum which is in close proximity to 665 nm.

The presently disclosed subject matter provides a method and a device for the assessment of the de-oxygenated hemoglobin concentration in tissue, $C_D$, making use of the selective wavelength-dependent light absorption of the multiple wavelengths in the spectrum of a red single LED (range 640-720 nm). The present invention also applies to a method and a device for the measurement of the oxygenated hemoglobin concentration in tissue, $C_O$, making use of the selective wavelength-dependent light absorption of the multiple wavelengths in the spectrum of an infrared single LED (range 820-880 nm).

These two wavelength regions, 640-720 nm for the measurement of $C_D$ and 820-880 nm for the measurement of $C_O$, are appropriate for the assessment of $C_D$ and $C_O$, because in the range of 640-720 nm, $\varepsilon_D$, the extinction coefficients for Hb strongly depends on $\lambda$ while $\varepsilon_O$, the extinction coefficients for $HbO_2$, is almost constant. In the range of 820-880 nm, $\varepsilon_O$ strongly depends on $\lambda$ while $\varepsilon_D$ is almost constant. In particular, the unique dependence of the hemoglobin extinction coefficients on the light wavelength in the 640-720 nm, that consists of steep declining slope of the extinction coefficient curve for ReHb curve and constant $HbO_2$ curve, provides a substantial means to assess $C_D$ with great sensitivity.

As explained above, since the shift to right in the spectrum of the normalized transmitted light for emitted LED light in the 640-720 nm range is because of the wavelength-dependence of $\varepsilon_D$, the amount of the shift can be used as a qualitative measure to the level of ReHb concentration in the examined tissue: changes in the spectral shift to right of the transmitted light are related to changes in ReHb concentration.

In view of the above, the presently disclosed subject matter provides a method for the measurement of oxygenation level of blood in a tissue. The method includes applying on a tissue light with a spectrum within wavelength-region of 640-720 nm and measuring the spectrum of the light transmitted through the tissue. Preferably the light is applied by utilizing a light-emitting-diode (LED). The spectrum emitted by the LED and the spectrum of the light transmitted through the tissue are analyzed. At least one parameter of the emitted spectrum is compared with the same parameter of the transmitted spectrum, such that this differentiating parameter expresses the changes in the intensity due to the absorption of deoxygenated hemoglobin.

The intensity changes are assessed with respect to at least one wavelength within the emitted and transmitted spectrum, which wavelength is selected such that the concentration of deoxygenated hemoglobin can be derived from these intensity changes.

In accordance with concentration of deoxygenated hemoglobin oxygenation level of the blood in the tissue is determined. It is appreciated by those skilled in the art that oxygenation level can include concentration of oxygenated hemoglobin, concentration of deoxygenated hemoglobin, and oxygen saturation.

According to an example, the parameter can be wavelength at the peak of the emitted and transmitted spectra 10a and 10b, and the differentiating parameter can be the difference between the wavelength of the peak 12a of the emitted spectrum 10a and the wavelength of peak 12b transmitted spectrum 10b.

Alternatively, the parameter can be weighted mean wavelength of the emitted and transmitted spectra 10a and 10b.

The differentiating parameter in this case can be the difference between the weighted mean wavelength of the emitted spectrum 10a and the weighted mean wavelength of the transmitted spectrum 10b. Another example of the parameter which can be analyzed is the mean extinction coefficient, and the differentiating parameter can be the difference between the mean extinction coefficient of the emitted spectrum 10a and the mean extinction coefficient of the transmitted spectrum 10b.

It would be appreciated that other differentiating parameters expressing the difference between the emitted and transmitted spectra can be derived, and that the spectra can be normalized so as to eliminate changes in the transmitted intensity which are not directly related to the decline of the extinction coefficient of the absorption of ReHb.

According to an example, in order to derive the oxygenation level from the differentiating parameter expressing the difference between the emitted and transmitted spectra, calibration methods may be utilized. I.e., for each selected differentiating parameter the value obtained for that parameter corresponds to a certain oxygenation level. It should be appreciated that according to the present method a single differentiating parameter may be sufficient to show the difference between the emitted and transmitted spectra 10a and 10b. For example, if the differentiating parameter is the difference between wavelength of the peak 12a of the emitted spectrum 10a and the wavelength of peak 12b transmitted spectrum 10b, the difference between the wavelength can have a value within a certain range, i.e., range of expected difference between the wavelength at the peaks 12a and 12b. Each value within the expected range corresponds to an oxygenation level in the blood.

In order to determine the correspondence between the value of the differentiating parameter and the oxygenation level known methods of near infrared spectroscopy may be utilized. Alternatively, the correspondence between the value of the differentiating parameter and the oxygenation level can be determined by utilizing venous and/or arterial pulse oximetry. It would be appreciated that such calibration needs to be done only to determine the correspondence between the differentiating parameter and the oxygenation level, and once such correspondence is achieved, measurements of the oxygenation level can be determined directly in accordance with the value obtained for the differentiating parameter.

Accordingly, the above method can be applied with a measuring device configured to assess the value of a predetermined differentiating parameter. The measuring device can include a microprocessor being preprogrammed with the correspondences between the expected values of a predetermined differentiating parameter and the oxygenation level. Thus, the measuring device can measure the predetermined differentiating parameter for each examinee and monitor for that examinee the oxygenation level corresponding to the value obtained for the differentiating parameter. Alternatively, the measuring device can measure the predetermined differentiating parameter for several examinees and provide the mean oxygenation level corresponding to the value obtained for the differentiating parameter measured in any subject.

Alternatively, the correspondence between the value of the differentiating parameter and the oxygenation level can be obtained by directly calculating the concentrations of oxygenated or de-oxygenated hemoglobin, $C_D$ or $C_O$, in the tissue (in units of mole per cc), depending on the wavelength range of the LED emission spectrum. These concentrations can be obtained from the modified Beer-Lambert Law (See Equation 2a and 2b above), as follows:

$$\ln\left(\frac{I_0}{I_t}\right)(\lambda) = G(\lambda) + \varepsilon_D C_D l_R(\lambda) + \varepsilon_O C_O l_{IR}(\lambda)$$ (hereinafter Equation [3])

where $I_0$ and $I_t$ are the incident and transmitted light, $\varepsilon_O$ and $\varepsilon_D$ are the extinction coefficients for $HbO_2$ and Hb, respectively, and $l_R(\lambda)$ and $l_{IR}(\lambda)$ are the pathlengths in tissue for the red light and the infrared light, respectively. $G(\lambda)$ is the attenuation due to scattering and absorption in tissue, which generally depends on the wavelength $\lambda$.

The pathlengths $l_R(\lambda)$ and $l_{IR}(\lambda)$ in the wavelength range of 640-720 nm depend on the wavelength, because of the dependence of the difference pathlength factor (DPF) on the wavelength, due to the dependence on the wavelength of the scattering and absorption in tissue. Since the dependence of the scattering and absorption by the tissue on the wavelength is moderate, both pathlengths $l_R(\lambda)$ and $l_{IR}(\lambda)$ can be considered constant in the small wavelength range of 640-720 nm.

As explained hereinabove, in the region of 640-720 nm the $HbO_2$ extinction coefficient is almost constant as a function of wavelength while the RcHb extinction coefficient is much greater than $HbO_2$ extinction coefficient and declines steeply with the wavelength. Hence, making use of Equation [3], the value of $C_D l(\lambda)$ can be derived from the slope of $$\ln\left(\frac{I_0}{I_t}\right)(\lambda)$$

as a function of $\varepsilon_D(\lambda)$, utilizing the fact that the dependence on wavelength of G, the attenuation by scattering, and $\varepsilon_O(\lambda) C_O l(\lambda)$, and the absorption by $HbO_2$, can be neglected relative to the dependence on wavelength of $\varepsilon_D(\lambda) C_D l(\lambda)$, the absorption by ReHb.

Figure 5:
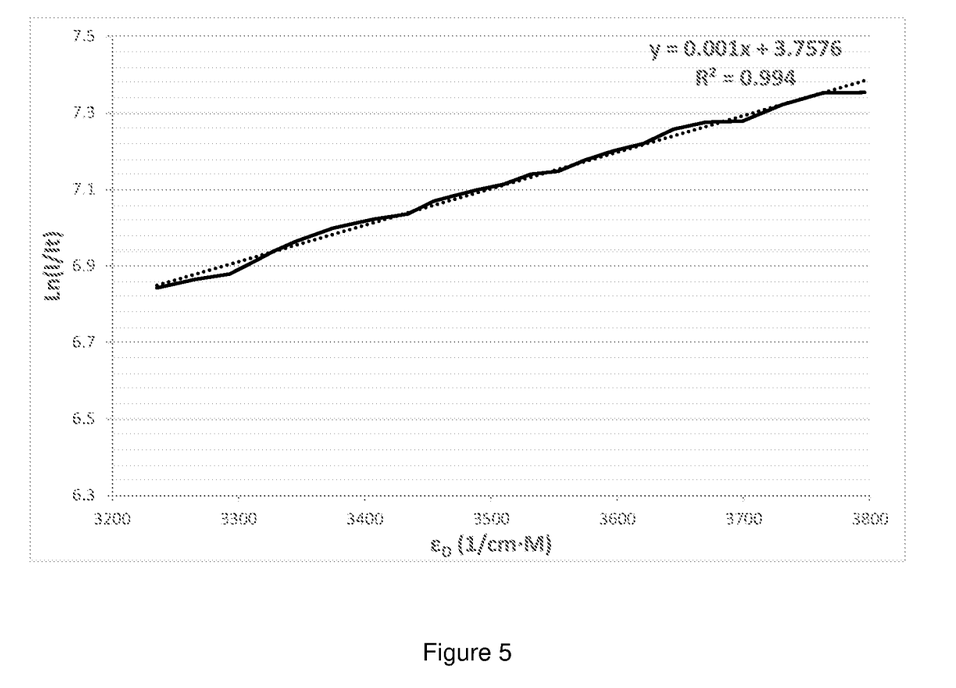

FIG. 5 presents curve of $$\ln\left(\frac{I_0}{I_t}\right)(\lambda)$$

as a function of $\varepsilon_D(\lambda)$, for one of the examinees. The value of $C_D l(\lambda)$ can be derived from the slope of $$\ln\left(\frac{I_0}{I_t}\right)(\lambda)$$

versus $\varepsilon_D(\lambda)$ curve, but the value of $l(\lambda)$ is not known. Rough approximation of $C_D$ can be obtained from the value $C_D l(\lambda)$ by substituting the value of the difference pathlength factor, which is about 5, as obtained in the literature (Nitzan 2000) assuming that the dependence on wavelength of $l(\lambda)$ can be neglected in the small wavelength range of 640-720 nm.

By monitoring spectral changes of the red LED as a function of time, changes in $C_D l(\lambda)$ due to performance of some maneuver or a physiological change can be derived. In general, the changes in $C_D l(\lambda)$ are because of changes in $C_D$ and not due to changes in $l(\lambda)$.

Changes in $C_O l(\lambda)$ can be obtained from the changes in $C_D l(\lambda)$ and measurement of changes in total hemoglobin concentration.

The above describes obtaining oxygenation level of blood in the tissue is determined by measuring $C_D l(\lambda)$ from the slope of $$\ln\left(\frac{I_0}{I_t}\right)(\lambda)$$

as a function of $\varepsilon_D(\lambda)$. This is where the LED light spectrum is primarily in the red region, 640-720 nm, or preferably in the region of 650-670 nm, where the $HbO_2$ extinction coefficient is almost constant while the ReHb extinction coefficient is much greater than $HbO_2$ extinction coefficient and is very sensitive to changes in the wavelength.

It is appreciated that alternatively, oxygenation level of blood in the tissue is determined by measuring $C_O l(\lambda)$ from the slope of $$\ln\left(\frac{I_0}{I_t}\right)(\lambda)$$

as a function of $\varepsilon_O(\lambda)$. For example, when the LED light spectrum is primarily in the infrared region 820-880 nm, where the ReHb extinction coefficient is almost constant while the $HbO_2$ extinction coefficient is greater and is more sensitive to changes in the wavelength, as shown in FIG. 2.

Those skilled in the art to which the presently disclosed subject matter pertains will readily appreciate that numerous changes, variations, and modifications can be made without departing from the scope of the invention, mutatis mutandis.

The invention claimed is:

1. A method for the measurement of an oxygenation level of blood in a tissue, the method comprising:
    emitting on the tissue only a spectrum of light in which oxygenated hemoglobin has a first extinction coefficient and de-oxygenated hemoglobin has a second extinction coefficient, and wherein said second extinction coefficient changes monotonically as a function of wavelength within said spectrum, and wherein the first extinction coefficient is substantially constant with respect to said second extinction coefficient;
    measuring a transmitted spectrum of light transmitted through the tissue;
    measuring a differentiating parameter expressing a change in at least one parameter of the emitted spectrum with respect to same parameter in the transmitted spectrum;
    calculating from said differentiating parameter concentration of de-oxygenated hemoglobin in accordance with dependence of said second extinction coefficient on wavelength within said spectrum;
    determining the oxygenation level of blood in the tissue, in accordance with said concentration of de-oxygenated hemoglobin.

2. The method in accordance with claim 1, wherein said spectrum is within 640-720 nm.

3. The method in accordance with claim 1, wherein said step of measuring the differentiating parameter includes measuring a difference between a wavelength at a peak of the emitted spectrum and a wavelength at a peak of the transmitted spectrum.

4. The method in accordance with claim 1, wherein said step of measuring the differentiating parameter includes measuring a difference between a weighted mean wavelength of the emitted spectrum and a weighted mean wavelength of the transmitted spectrum.

5. The method in accordance with claim 1, wherein said step of measuring the differentiating parameter includes measuring a difference in mean extinction coefficients for the emitted and transmitted spectra.

6. The method in accordance with claim 1, wherein said step of calculating the concentration of the de-oxygenated hemoglobin is carried out by predetermined calibration comparing derived values of said differentiating parameter and a corresponding oxygenation level obtained by means of another method.

7. The method in accordance with claim 6, wherein said another method includes near infrared spectroscopy.

8. The method in accordance with claim 6, where said another method includes venous and/or arterial pulse oximetry.

9. The method in accordance with claim 1, wherein said differentiating parameter is $$\ln\left(\frac{I_0}{I_t}\right)(\lambda),$$

and wherein said step of calculating the concentration of the de-oxygenated hemoglobin in the tissue is carried out by utilizing the equation:

$$\ln\left(\frac{I_0}{I_t}\right)(\lambda) = \varepsilon_D C_D l_R(\lambda).$$

10. The method in accordance with claim 9 wherein the spectrum has a width configured such that changes in scattering constant as a function of wavelengths within the spectrum are negligible with respect to changes in said second extinction coefficient as a function of wavelengths within said spectrum.

11. A device for measurement of an oxygenation level of blood in a tissue, the device comprising:
a light source configured for emitting on the tissue only a spectrum of light in which oxygenated hemoglobin has a first extinction coefficient and de-oxygenated hemoglobin has a second extinction coefficient, and wherein said second extinction coefficient changes monotonically as a function of wavelength within said spectrum, and wherein the first extinction coefficient is substantially constant with respect to said second extinction coefficient;
a detector for detecting a transmitted spectrum of light emitted from said light source and transmitted through the tissue;
a controller configured for measuring a differentiating parameter expressing a change in at least one parameter of the emitted spectrum with respect to same parameter in the transmitted spectrum; said controller being further configured for calculating from said differentiating parameter concentration of de-oxygenated hemoglobin in accordance with dependence of said second extinction coefficient on wavelength within said spectrum and for determining the oxygenation level of blood in the tissue in accordance with said concentration of de-oxygenated hemoglobin.

12. The device of claim 11, wherein said differentiating parameter is a difference between a wavelength at a peak of the emitted spectrum and a wavelength at a peak of the transmitted spectrum.

13. The device of claim 11, wherein said differentiating parameter is a difference between a weighted mean wavelength of the emitted spectrum and a weighted mean wavelength of the transmitted spectrum.

14. The device of claim 11, wherein said differentiating parameter is a difference in mean extinction coefficients for the emitted and transmitted spectra.

15. The device of claim 11, wherein said controller includes predetermined calibration data between derived values of said differentiating parameter and a corresponding oxygenation level obtained by means of another device.

16. The device of claim 15, wherein said another device is a near infrared spectrometer.

17. The device of claim 15, where said another device is a venous and/or arterial pulse oximeter.

18. The device of claim 11, wherein said differentiating parameter is $$\ln\left(\frac{I_0}{I_t}\right)(\lambda)$$

and wherein said controller is configured for determining the oxygenation level of blood in the tissue by utilizing the equation:

$$\ln\left(\frac{I_0}{I_t}\right)(\lambda) = \varepsilon_D C_D l_R(\lambda).$$

19. A method for the measurement of a concentration of an oxygenated hemoglobin in blood in a tissue, the method comprising:
emitting on the tissue only a spectrum of light in which oxygenated hemoglobin has a first extinction coefficient and de-oxygenated hemoglobin has a second extinction coefficient and wherein said first extinction coefficient changes monotonically as a function of wavelength within said spectrum, and wherein said second extinction coefficient is substantially constant with respect to said first extinction coefficient;
detecting a transmitted spectrum of light transmitted through the tissue;
measuring a differentiating parameter expressing a change in at least one parameter of the emitted spectrum with respect to same parameter in the transmitted spectrum;
calculating from said differentiating parameter concentration of oxygenated hemoglobin in accordance with dependence of said first extinction coefficient on wavelength within said spectrum;
determining oxygenation level of blood in the tissue, in accordance with said concentration of oxygenated hemoglobin.

20. The method in accordance with claim 19 wherein said spectrum is within 820-880 nm.

21. The method in accordance with claim 19 wherein said spectrum has a width configured such that changes in scattering constant as a function of wavelengths within the spectrum are negligible with respect to changes in said first extinction coefficient as a function of wavelengths within said spectrum.

22. The method in accordance with claim 19, wherein said step of calculating the concentration of the oxygenated hemoglobin is carried out by predetermined calibration comparing derived values of said differentiating parameter and a corresponding oxygenation level obtained by near infrared spectroscopy, or venous and/or arterial pulse oximetry.

23. The method in accordance with claim 19, wherein said differentiating parameter is $$\ln\left(\frac{I_0}{I_t}\right)(\lambda),$$

and wherein said step of calculating the concentration of the oxygenated hemoglobin in the tissue is carried out by utilizing the equation:

$$\ln\left(\frac{I_0}{I_t}\right)(\lambda) = \varepsilon_o C_o l_{IR}(\lambda).$$

* * * * *